United States Patent
Wei

(10) Patent No.: US 11,913,965 B2
(45) Date of Patent: Feb. 27, 2024

(54) SANDWICH ASSAY FOR SMALL MOLECULES

(71) Applicant: Siemens Healthcare Diagnostics Inc., Tarrytown, NY (US)

(72) Inventor: Tie Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 256 days.

(21) Appl. No.: 17/249,767

(22) Filed: Mar. 12, 2021

(65) Prior Publication Data

US 2021/0199677 A1 Jul. 1, 2021

Related U.S. Application Data

(63) Continuation of application No. 15/770,925, filed as application No. PCT/US2016/056551 on Oct. 12, 2016, now abandoned.

(60) Provisional application No. 62/247,970, filed on Oct. 29, 2015.

(51) Int. Cl.
*G01N 33/94* (2006.01)
*G01N 33/531* (2006.01)

(52) U.S. Cl.
CPC ....... *G01N 33/9493* (2013.01); *G01N 33/531* (2013.01); *G01N 2470/04* (2021.08)

(58) Field of Classification Search
CPC ............ G01N 2470/04; G01N 33/531; G01N 33/9493
See application file for complete search history.

(56) References Cited

U.S. PATENT DOCUMENTS

| | | | |
|---|---|---|---|
| 8,586,322 B2 | 11/2013 | Wei | |
| 9,121,859 B2 | 9/2015 | Zheng et al. | |
| 11,377,483 B2* | 7/2022 | Zheng | C07K 16/44 |
| 2004/0198953 A1 | 10/2004 | Yatscoff et al. | |
| 2006/0099654 A1 | 5/2006 | Huster | |
| 2006/0246518 A1* | 11/2006 | Chen | G01N 33/9493 435/7.5 |
| 2006/0257957 A1 | 11/2006 | Drengler et al. | |
| 2013/0236918 A1 | 9/2013 | Wei | |
| 2014/0154700 A1 | 6/2014 | Teng et al. | |
| 2014/0308751 A1 | 10/2014 | Wei et al. | |
| 2017/0362305 A1 | 12/2017 | Zheng | |
| 2022/0024946 A1* | 1/2022 | Wei | C07D 498/18 |
| 2022/0229049 A1* | 7/2022 | Wei | G01N 33/54393 |

FOREIGN PATENT DOCUMENTS

| | | |
|---|---|---|
| EP | 2180323 | 4/2010 |
| JP | 2001518784 | 10/2001 |
| WO | 0022000 | 4/2000 |
| WO | 2008082982 | 7/2008 |
| WO | 2016100116 | 6/2016 |

OTHER PUBLICATIONS

European Office Action of European Application No. 16860497.3 dated Mar. 19, 2019.
International Search Report and Written Opinion of International Application No. PCT/US2016/056551 dated Jan. 10, 2017.
European Search Report and Written Opinion of European Application No. 16860497 dated Jul. 4, 2018.
Wei et al., "Sandwich Assay for Tacrolimus Using 2 Antitacrolimus Antibodies"; Clinical Chemistry 60:4; 2014; pp. 621-630.
Gounden et al., "Tacrolimus Measurement: Building a Better Immunoassay", Clinical Chemistry., vol. 60, No. 4, Jan. 10, 2014 (Jan. 10, 2014), pp. 575-576.
Freudenberger et al., "Recent Advances in Therapeutic Drug Monitoring of Immunosuppressive Drugs"; TRAC Trends in Analytical Chemistry, vol. 79, May 1, 2016 (May 1, 2016), pp. 257-268.
Omi et al., "Noncompetitive Immunoassay Detection System for Haptens on the Basis of Antimetatype Antibodies", Clinical Chemistry., vol. 61, No. 4, Feb. 18, 2015 (Feb. 18, 2015), pp. 627-635.
Quinton et al., "Toward the Limits of Sandwich Immunoassay of Very Low Molecular Weight Molecules", Feb. 24, 2010, Analytical Chemistry, 2010, 82 (6), pp. 2536-2540.
Marvin H. Goodrow et al: "Strategies for Immunoassay Hapten Design"; Immunoanalysis of Agrochemicals; Nelson J et al. ACS Symposium Series, vol. 586 Chapter 9; pp. 119-139, (1995).
Szurdoki et al.:; "Important Factors in Hapten Design and Enzyme-Linked Immunosorbent Assay Development"; in Immunoanalysis of Agrochemicals; Nelson J et al. ACS Symposium Series, vol. 586 Chapter 4, pp. 39-63, (1995).

* cited by examiner

*Primary Examiner* — Galina M. Yakovleva

(57) ABSTRACT

Methods are disclosed for a sandwich assay for a small molecule having a molecular weight of about 500 to about 2,500. The method comprises the use of a first antibody that binds to the small molecule and a second antibody that binds to the small molecule at a portion of the small molecule other than a portion to which the first antibody binds. The second antibody is prepared from an immunogen that comprises a hapten that is not the small molecule or a derivative of the small molecule wherein the hapten comprises a moiety that is structurally similar to that of the second portion of the small molecule. The antibodies may be employed in sandwich assays for the small molecule.

11 Claims, 7 Drawing Sheets

I

Sirolimus

II

Everolimus

III

Tacrolimus

III

SANDWICH ASSAY FOR SMALL MOLECULES

The subject application is a continuation of U.S. Ser. No. 15/770,925, filed Apr. 25, 2018; which is a U.S. national stage application under 35 USC § 371 of International Application No. PCT/US2016/056551, filed Oct. 12, 2016; which claims benefit under 35 USC § 119(e) of U.S. Provisional Application No. 62/247,970, filed Oct. 29, 2015. The entire content of the above-referenced patent application is hereby expressly incorporated herein by reference.

BACKGROUND

The invention relates to compounds, methods and kits for the determination of small molecules, in samples, such as patient samples, known or suspected to contain one or more of such small molecules. In some aspects the invention relates to sandwich assays for small molecules such as, for example, immunosuppressant drugs.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are therapeutic drugs that are carefully administered to transplant recipients in order to help prevent allograft rejection of non-self tissue. Immunosuppressive drugs can be classified as follows: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins, the latter of which specifically bind, for example, tacrolimus or sirolimus.

Two most commonly administered immunosuppressive drugs to prevent organ rejection in transplant patients are cyclosporine (CSA) and FK-506 (FK or tacrolimus). Another drug that finds use as an immunosuppressant in the United States and other countries is sirolimus, also known as rapamycin. Derivatives of sirolimus are also useful as immunosuppressants. Such derivatives include, for example, everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because distribution and metabolism of an immunosuppressant drug can vary greatly between patients and because of a wide range and severity of adverse reactions, accurate monitoring of the drug level is essential. Assays for accurately monitoring drug level in patients are subject to cross-reactivity with drug analogs such as metabolites, which interfere with accurate measurement of drug level in a patient.

There is, therefore, a continuing need to develop fast and accurate diagnostic methods to measure levels of small molecules such as, for example, immunosuppressant drugs or derivatives thereof in patients. The methods should be capable of being fully automated and should selectively detect the parent molecule while minimizing inaccuracies resulting from the cross-reactivity of its metabolites or from constituents in a sample suspected of containing the small molecule.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Figure 1:
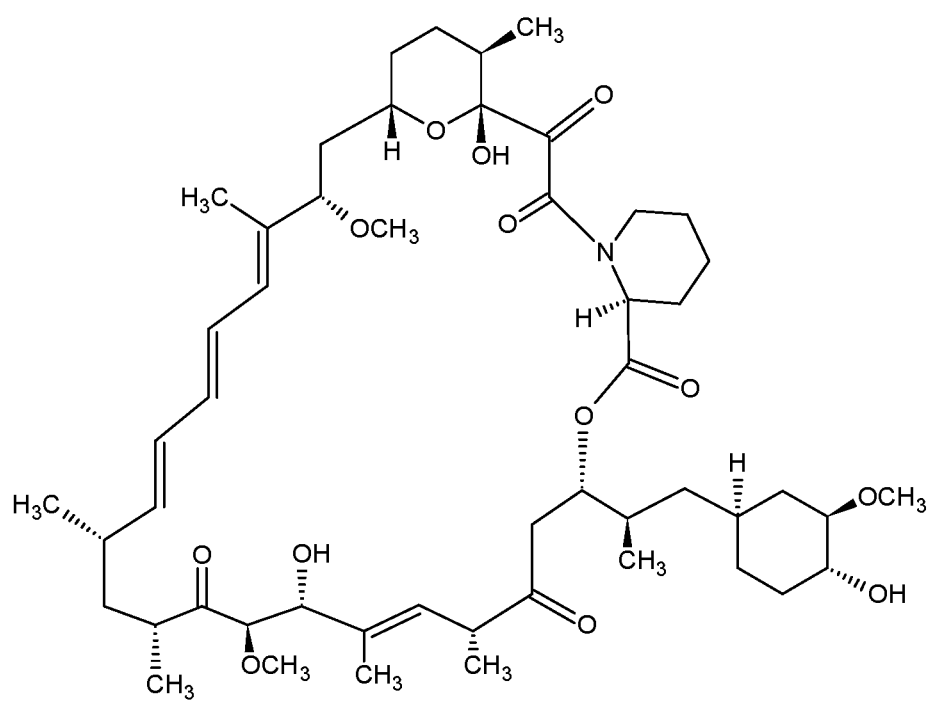
FIG. 1 is a chemical formula for sirolimus (I).
Figure 2:
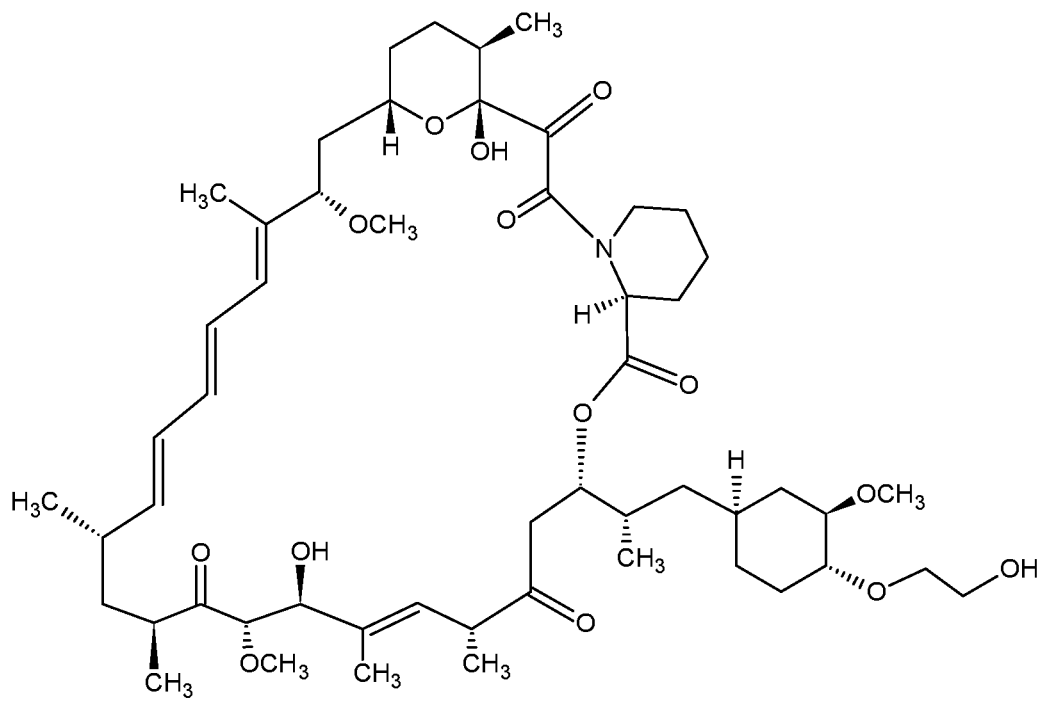
FIG. 2 is a chemical formula for everolimus (II).
Figure 3:
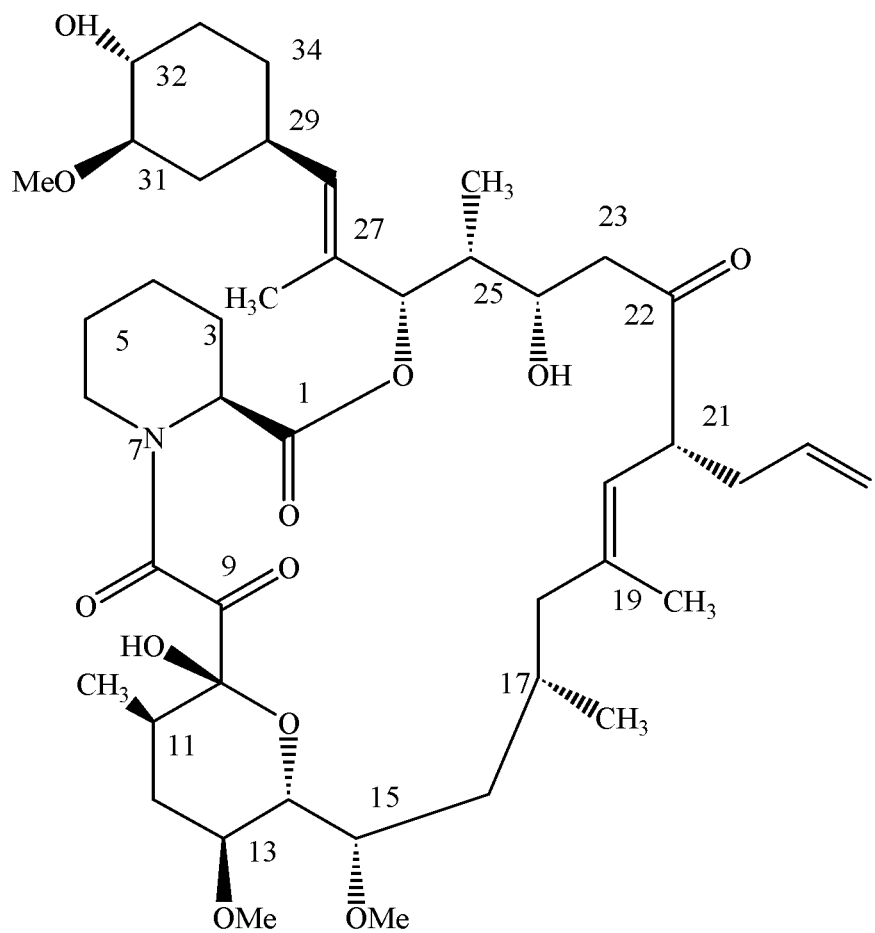
FIG. 3 is a chemical formula for tacrolimus (III).

The present inventors have discovered that binding partners such as, for example, antibodies, can be designed that specifically bind simultaneously to separate portions of small molecules. This discovery is surprising because small molecules are haptens, which are relatively small molecules (molecular weight (daltons) less than about 2,500, or less than about 2000, or less than about 1500, or less than about 1000) and are not considered to have more than one site to which an antibody can bind. In accordance with the principles described herein, at least two different binding partners can be prepared, which bind to separate portions of a small molecule at the same time. The first binding partner binds to and is specific for a first portion of the small molecule. The second binding partner binds to the small molecule at a second portion of the small molecule other than the first portion, wherein the second binding partner is prepared from an immunogen that comprises a hapten that is not the small molecule or a derivative of the small molecule and wherein the hapten of the immunogen comprises a moiety that is structurally similar to that of the second portion of the small molecule.

Some examples in accordance with the principles described herein are directed to methods of determining a presence and/or amount of a small molecule having a molecular weight of about 500 to about 2,500 in a sample suspected of containing the small molecule. A combination that comprises the sample, a first binding partner that binds to and is specific for a first portion of the small molecule, and a second binding partner that binds to the small molecule at a second portion of the small molecule other than the first portion is formed in a medium. The second binding partner is prepared from an immunogen that comprises a hapten that is not the small molecule or a derivative of the small molecule. The hapten of the immunogen comprises a moiety that is structurally similar to that of the second portion of the small molecule. The medium is incubated under conditions for binding of the first binding partner and the second binding partner to the small molecule. The medium is examined for the presence of an immunocomplex comprising the small molecule, the first binding partner and the second binding partner, the presence and/or amount of the immunocomplex indicating the presence and/or amount of the small molecule in the sample.

Some examples in accordance with the principles described herein are directed to methods of determining a presence and/or amount of an immunosuppressant drug in a sample suspected of containing the immunosuppressant drug. The method comprises providing in combination in a medium (i) the sample, (ii) a first antibody that binds to and is specific for a first portion of the immunosuppressant drug, and (iii) a second antibody that binds to the immunosuppressant drug at a second portion of the immunosuppressant drug other than the first portion. The second antibody is prepared from an immunogen that comprises a hapten that is not the immunosuppressant drug or a derivative thereof. The hapten of the immunogen comprises a moiety that is structurally similar to that of the second portion of the immunosuppressant drug. The medium is incubated under conditions for binding of the first antibody and the second antibody to the immunosuppressant drug. The medium is examined for the presence of an immunocomplex comprising the immunosuppressant drug, the first antibody and the second antibody, the presence and/or amount of the immunocomplex indicating the presence and/or amount of the immunosuppressant drug in the sample.

Some examples in accordance with the principles described herein are directed to methods of determining a presence and/or amount of an immunosuppressant drug selected from the group consisting of sirolimus or everolimus in a sample suspected of containing the immunosuppressant drug. A combination is formed in a medium wherein the combination comprises the sample, a first monoclonal antibody that binds to and is specific for a first portion of the immunosuppressant drug, and a second monoclonal antibody that binds to the immunosuppressant drug at a second portion of the immunosuppressant drug other than the first portion, wherein the second monoclonal antibody is prepared from an immunogen that comprises tacrolimus or a derivative of tacrolimus. The medium is incubated under conditions for binding of the first monoclonal antibody and the second monoclonal antibody to the immunosuppressant drug. The medium is examined for the presence of an immunocomplex comprising the immunosuppressant drug, the first antibody and the second antibody, the presence and/or amount of the immunocomplex indicating the presence and/or amount of the immunosuppressant drug in the sample.

The term "small molecule" refers to a molecule having a molecular weight of about 150 to about 2,500, or about 150 to about 2,000, or about 150 to about 1,500, or about 150 to about 1,000, or about 150 to about 500, or about 300 to about 2,000, or about 300 to about 1,500, or about 300 to about 1,000, or about 500 to about 2,000, or about 500 to about 1,500, or about 500 to about 1,000, for example. For the most part, small molecules do not elicit an immune response by themselves.

The phrase "binding partner for a small molecule" refers to a molecule that binds specifically to the small molecule and does not bind to any significant degree to other substances that would distort the analysis for the small molecule. Furthermore, the binding partner for the small molecule binds specifically to a certain domain of the small molecule. Specific binding involves the specific recognition of one of two different molecules, or two different domains of a small molecule, for the other compared to substantially less recognition of other molecules or other domains of a small molecule. On the other hand, non-specific binding involves non-covalent binding between molecules that is relatively independent of specific surface structures. Non-specific binding may result from several factors including hydrophobic interactions between molecules. The binding partners may be, but are not limited to, antibodies including monoclonal antibodies, receptors for molecules with similar chemical structures, plasma transporter proteins such as albumin, and lipoproteins, for example.

The phrase "antibody for a small molecule" refers to an antibody that binds specifically to the small molecule and does not bind to any significant degree to other substances that would distort the analysis for the small molecule. Furthermore, the antibody for the small molecule binds specifically to a certain portion or domain of the small molecule.

A small molecule, to which examples in accordance with the principles described herein may be applied, has spatially separate binding domains for the antibodies. The small molecule may be linear or it may comprise one or more rings, for example, two rings, or three rings, or four rings, or five rings, or more. The binding domains on the small molecule should be separated such that two different binding partners can bind simultaneously to the small molecule without interfering with the binding of each other to form a three-member complex (or immunocomplex) wherein each binding partner binds to an extent necessary so that a sufficiently stable complex is formed comprising the two binding partners and the small molecule. The complex is considered sufficiently stable when the complex remains intact during an assay so that the complex can be detected and the amount of the complex accurately reflects the amount of a small molecule analyte in a sample. The stable complex permits an accurate and sensitive assay for the small molecule analyte.

In some examples the small molecule comprises at least one large ring, which is a 15-50 membered ring, or a 15-45 membered ring, or a 15-40 membered ring, or a 15-35 membered ring, or a 15-30 membered ring, or a 15-25 membered ring, or a 15-20 membered ring, or a 20-50 membered ring, or a 20-45 membered ring, or a 20-40 membered ring, or a 20-35 membered ring, or a 20-30 membered ring, or a 20-25 membered ring, or a 25-50 membered ring, or a 25-45 membered ring, or a 25-40 membered ring, or a 25-35 membered ring, or a 25-30 membered ring, or a 30-50 membered ring, or a 30-45 membered ring, or a 30-40 membered ring, for example. The atoms forming the ring are primarily carbon and may also include, but are not limited to, oxygen, nitrogen and sulfur, for example. The large ring may also comprise 1-5, or 1-4, or 1-3 or 1-2, or 2-5, or 2-4, or 2-3, small rings, which are 5-7 membered rings or 5-6 membered rings. Some of the atoms of the small rings may be part of the large ring.

In some examples, the small molecule comprises a three dimensional conformation with one or more unique chemical functional groups that allow different binding partners to be prepared where at least two different binding partners can approach and bind to different binding domains on the small molecule without interfering with one another. The unique chemical functional groups include, by way of illustration and not limitation, carbon-carbon double bonds, carbon-carbon triple bonds, carbonyl groups, imine groups, carboxyl groups, hydroxyl groups, amine groups, amide groups, ester groups and ether groups, for example, and combinations of two or more of the above. The chemical functional groups may be unconjugated or conjugated. The term "conjugated" refers to contiguous atoms that have available p-orbitals such that electrons can be delocalized over the contiguous atoms. Examples of conjugated atoms include, but are not limited to, one, two, three, four, or five or more conjugated carbon-carbon double bonds (vinyl groups); one, two, three, four, or five or more conjugated carbon-carbon triple bonds; a combination of one, two, three, four, or five or more conjugated carbon-carbon double bonds, carbon-carbon triple bonds, imine groups, carbonyl groups, and anions, for example. In some examples, the chemical functional groups provide a particular spatial conformation for the small molecule.

In some examples the small molecule is a macrolide. In some examples the macrolide is an immunosuppressant drug. The term "immunosuppressant drugs" includes those that act on immunophilin such as, but not limited to, cyclosporin (including cyclosporin A, cyclosporin B, cyclosporin C, cyclosporin D, cyclosporin E, cyclosporin F, cyclosporin G, cyclosporin H, cyclosporin I), tacrolimus (FR-900506, FK506, PROGRAF®), sirolimus (rapamycin, RAPAMUNE®), and derivatives of the above such as, but not limited to, Everolimus (RAD, CERTICAN®), for example.

As mentioned above, some examples in accordance with the principles described herein are directed to methods of designing antibodies for a sandwich assay for a small molecule having a molecular weight of about 500 to about 2,500. The method comprises preparing a first antibody that binds to a portion or domain of the small molecule, and preparing a second antibody that binds to the small molecule at a portion or domain of the small molecule other than a portion or domain to which the first antibody binds. The second antibody is prepared from an immunogen that comprises a hapten that is not the small molecule or a derivative of the small molecule where the hapten comprises a moiety that is structurally similar to that of the second portion of the small molecule.

The phrase "structurally similar" means that one moiety has the same or similar structural or spatial characteristics as another moiety such that both moieties exhibit a binding affinity to an antibody that is at least $10^5$ liters per mole, or least $10^6$ liters per mole, or least $10^7$ liters per mole, or least $10^8$ liters per mole, or least $10^9$ liters per mole, for example. In some examples, an antibody exhibits substantially the same binding affinity to each moiety, which means that the binding affinity of one moiety for the antibody does not differ from the binding affinity for the other moiety by more than $10^3$, or by more than $10^2$, or by more than 10, for example.

The phrase "hapten that is not the small molecule" refers to a compound other than small molecule or other than a derivative of the small molecule. The phrase "derivative of the small molecule" refers to a small molecule that is modified by formation of an ester, an amide, or an ether, for example, or is modified by hydrolysis of an ester, an amide, or an ether, for example. The hapten that is not the small molecule comprises a moiety that is structurally similar to that of the portion (second portion) of the small molecule other than the portion of the small molecule to which the first antibody binds. In some examples the small molecule is sirolimus or everolimus and the hapten of the immunogen that is not the small molecule is, by way of illustration and not limitation, tacrolimus or a derivative of tacrolimus, for example. The immunogen comprises the hapten that is not the small molecule linked to an immunogenic carrier and may be used in preparing antibodies in accordance with the principles described herein.

Preparation of monoclonal antibodies that simultaneously bind to two different domains on a small molecule enables the use of such antibodies in sandwich assays in which the small molecule is simultaneously bound by the two different antibodies to form an immunocomplex. The ability to perform sandwich assays on small molecules enhances the sensitivity of an assay for the small molecule. In addition, in the case of sandwich assays involving one monoclonal antibody bound to a support, the assay may be conducted in the presence of impurities and interfering substances of a sample because the support can be separated from the sample and washed after small molecule has been allowed to bind to the monoclonal antibody of the support but before introduction of the second monoclonal antibody.

Antibodies may include a complete immunoglobulin or fragment thereof, which immunoglobulins include the various classes and isotypes, such as IgA, IgD, IgE and IgM, for example. Fragments thereof may include Fab, Fv and F(ab')$_2$, Fab', for example. In addition, aggregates, polymers, and conjugates of immunoglobulins or their fragments can be used where appropriate so long as binding affinity for a particular molecule is maintained.

Antibodies in accordance with the principles described herein may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

Monoclonal antibodies can be prepared by techniques that are well known in the art such as preparing continuous hybrid cell lines and collecting the secreted protein (somatic cell hybridization techniques). Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites. This approach involves cloning and expressing nucleotide sequences or mutagenized versions thereof coding at least for the amino acid sequences required for specific binding of natural antibodies.

In one approach for the production of monoclonal antibodies, a first step includes immunization of an antibody-producing animal such as a mouse, a rat, a goat, a sheep, or a cow with an immunogen in accordance with the principles described herein. Immunization can be performed with or without an adjuvant such as complete Freund's adjuvant or other adjuvants such as monophosphoryl lipid A and synthetic trehalose dicorynomycolate adjuvant. A next step includes isolating spleen cells from the antibody-producing animal and fusing the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. A next step includes selection of the fused cells, typically by selection in HAT medium. A next step includes screening the cloned hybrids for appropriate antibody production using immunoassays such as enzyme-linked immunosorbent assay (ELISA) or other immunoassays appropriate for screening.

An antibody (prepared from an immunogen in accordance with the principles described herein) with the requisite specificity may be selected by screening methodologies, which include, by way of illustration and not limitation, ELISA, dot blots, Western analysis, and Surface Plasmon Resonance, for example. In this manner an antibody is obtained that binds to a domain of a small molecule of interest and does not bind to any detectable degree to other domains of the small molecule or to other molecules that are not of interest in a particular assay. In some examples in accordance with the principles described herein, an antibody that binds to a domain of a small molecule of interest has a binding affinity for the domain of the small molecule of interest of about $10^7$ to about $10^{14}$ liters/mole, or about $10^7$ to about $10^{11}$ liters/mole, or about $10^7$ to about $10^{12}$ liters/mole, or about $10^8$ to about $10^{14}$ liters/mole, or about $10^8$ to about $10^{11}$ liters/mole, or about $10^8$ to about $10^{12}$ liters/mole, for example. The phrase "any detectable degree" means that the antibody that specifically binds to a domain of a small molecule of interest has a binding affinity for other domains of the small molecule of interest or for other molecules that are not of interest of less than about $10^4$ liters/mole, or less than about $10^3$ liters/mole, or less than about $10^2$ liters/mole, or less than about 10 liters/mole, for example.

The term "hapten" refers to compounds that do not elicit an immune response unless linked to large molecule or immunogenic carrier that does illicit an immune response in order to raise antibodies. Haptens are compounds capable of binding specifically to corresponding antibodies, but do not themselves act as immunogens (or antigens) for preparation of the antibodies. Haptens have a molecular weight of about 150 to about 2,500.

The term "immunogenic carrier" means a group or moiety which, when conjugated to a hapten and injected into a mammal or otherwise employed as an immunogen, induces an immune response and elicits production of antibodies that bind to the hapten. Immunogenic carriers are also sometimes referred to as antigenic carriers. In some examples in accordance with the principles described herein, immunogens comprising immunogenic carriers, including poly(amino acid) and non-poly(amino acid) immunogenic carriers, linked to a small molecule at a particular position are synthesized and used to prepare antibodies in accordance with the principles described herein.

The molecular weight range (in Daltons) for poly(amino acids) that are immunogenic carriers is about 5,000 to about 10,000,000, or about 20,000 to about 600,000, or about 25,000 to about 250,000 molecular weight, for example. Poly(amino acid) immunogenic carriers include proteins such as, for example, albumins, serum proteins, e.g., globulins, ocular lens proteins and lipoproteins. Illustrative proteins include, but are not limited to, bovine serum albumin (BSA), keyhole limpet hemocyanin (KLH), egg ovalbumin, and bovine gamma-globulin (BGG), thyroglobulin, ovalbumin or fibrinogen, for example. In one illustrative example, the protein is KLH; in another illustrative example, the protein is BSA. Non-poly(amino acid) immunogenic carriers include polysaccharides, nucleic acids and particles (biologic and synthetic materials). A wide variety of immunogenic carriers are disclosed in Davalian, et al., U.S. Pat. No. 5,089,390, column 4, line 57 to column 5, line 5, which is incorporated herein by reference.

As mentioned above, the immunogenic carrier may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

As mentioned above, in some examples in accordance with the principles described herein, the immunogenic carrier may be linked to a compound of the immunogen that is not the small molecule at a predetermined position on the compound by means of a linking group. In some examples, the linking group may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. Part or all of the linking group may be a portion of the molecule being linked to the compound such as, but not limited to, an amino acid residue on a poly(amino acid), for example. In some examples, the linking group comprises an oxime functionality.

The number of heteroatoms in the linking group may be in the range from 0 to about 20, or 1 to about 15, or about 2 to about 10. The linking group may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. One specific embodiment of a linking group comprising heteroatoms is an oxime functionality as mentioned above.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid is linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking groups are well known in the art; see, for example, Cautrecasas, *J. Biol. Chem.* (1970) 245:3059.

Sirolimus as a Specific Example

The following specific description is by way of illustration of, and not as a limitation on, the scope of the present invention. Selection of immunosuppressant drugs, and sirolimus in particular, is also by way of illustration and not limitation as the present invention has general application to detection of any small molecule that has spatially separated regions to which antibodies can be raised against an immunogen that is not the small molecule and to which such raised antibodies will bind specifically during an assay for the small molecule.

Monoclonal antibodies may be prepared that bind to separate portions of the sirolimus molecule (FIG. 1). The separate portions to which the monoclonal antibodies bind may be determined, for example, by cross-reactivity studies using, for example, metabolites of sirolimus, or modified sirolimus.

Figure 4:
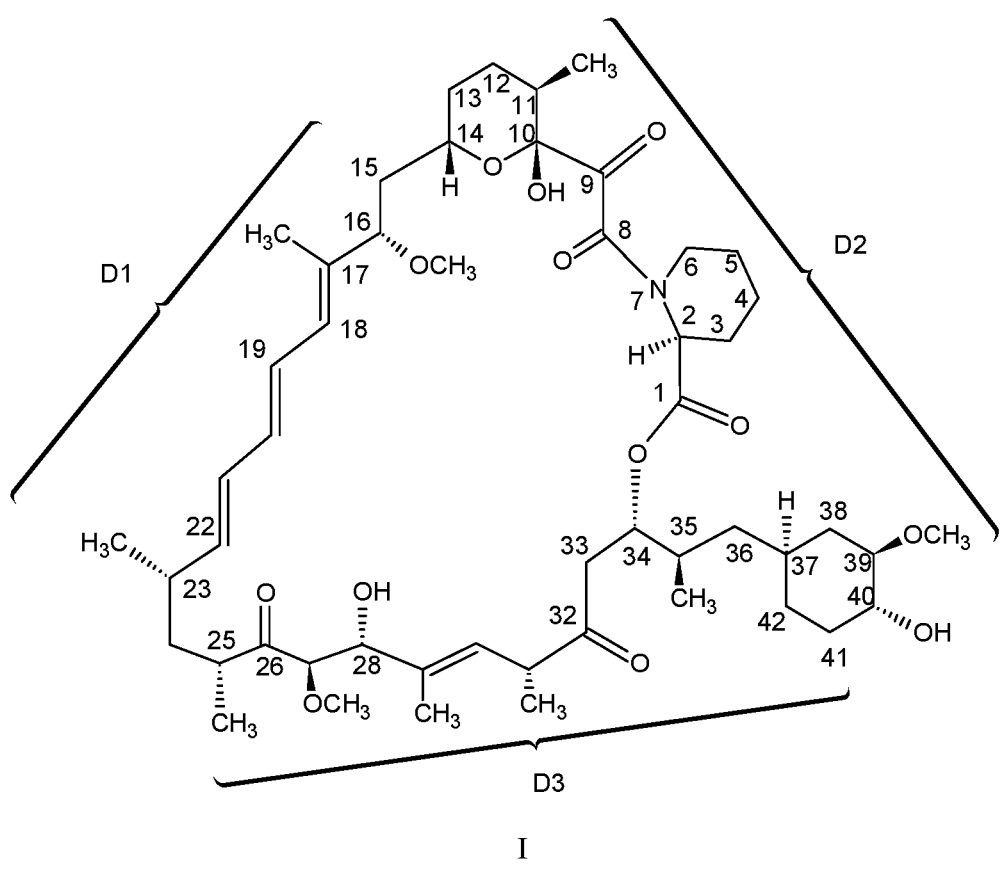
FIG. 4 is the chemical formula of FIG. 1 with numbering and depicting portions of the molecule to which monoclonal antibodies can be prepared in accordance with the principles described herein.

Referring to FIG. 4, by way of illustration and not limitation, three potential binding domains on the sirolimus molecule are indicated as D1, D2 and D3. Binding domain D1 extends approximately from ring atom 15 to ring atom 21 and includes a triene moiety from ring atom 17 to ring atom 22. Binding domain D2 extends approximately from the methyl group on atom 11 to the methoxy group on atom 39. Binding domain D3 extends from the methyl group on ring atom 25 to atom 41. In one example in accordance with the principles described herein, a first antibody is prepared that binds to D1 of the sirolimus molecule. A second antibody is prepared that binds to sirolimus at a portion of the small molecule other than a portion to which the first antibody binds, which in this example is either domain D2 or domain D3 of the sirolimus molecule. The second antibody is prepared from an immunogen that comprises a hapten that is not the small molecule or a derivative of the small molecule. The immunogen comprises a hapten that comprises a moiety that is structurally similar to that of the second portion of the small molecule.

The above discussion also applies to the detection of everolimus, the structure of which is substantially similar to that of sirolimus.

Preparation of Antibodies for Sandwich Assay for Sirolimus

By way of illustration and not limitation, in one approach anti-sirolimus antibody is prepared from an immunogen that comprises sirolimus. The anti-sirolimus antibody binds to domain region D1 of sirolimus as can be determined by, for example, a screening assay as described hereinbelow.

In one example, by way of illustration and not limitation, a first monoclonal antibody is prepared that binds to a portion of sirolimus represented by domain region D1. This first monoclonal antibody may be prepared using compound Va ($R^5$ is BSA), for example, as an immunogen in the methods of antibody production described below (see FIGS. 6 and 7).

Figure 6:
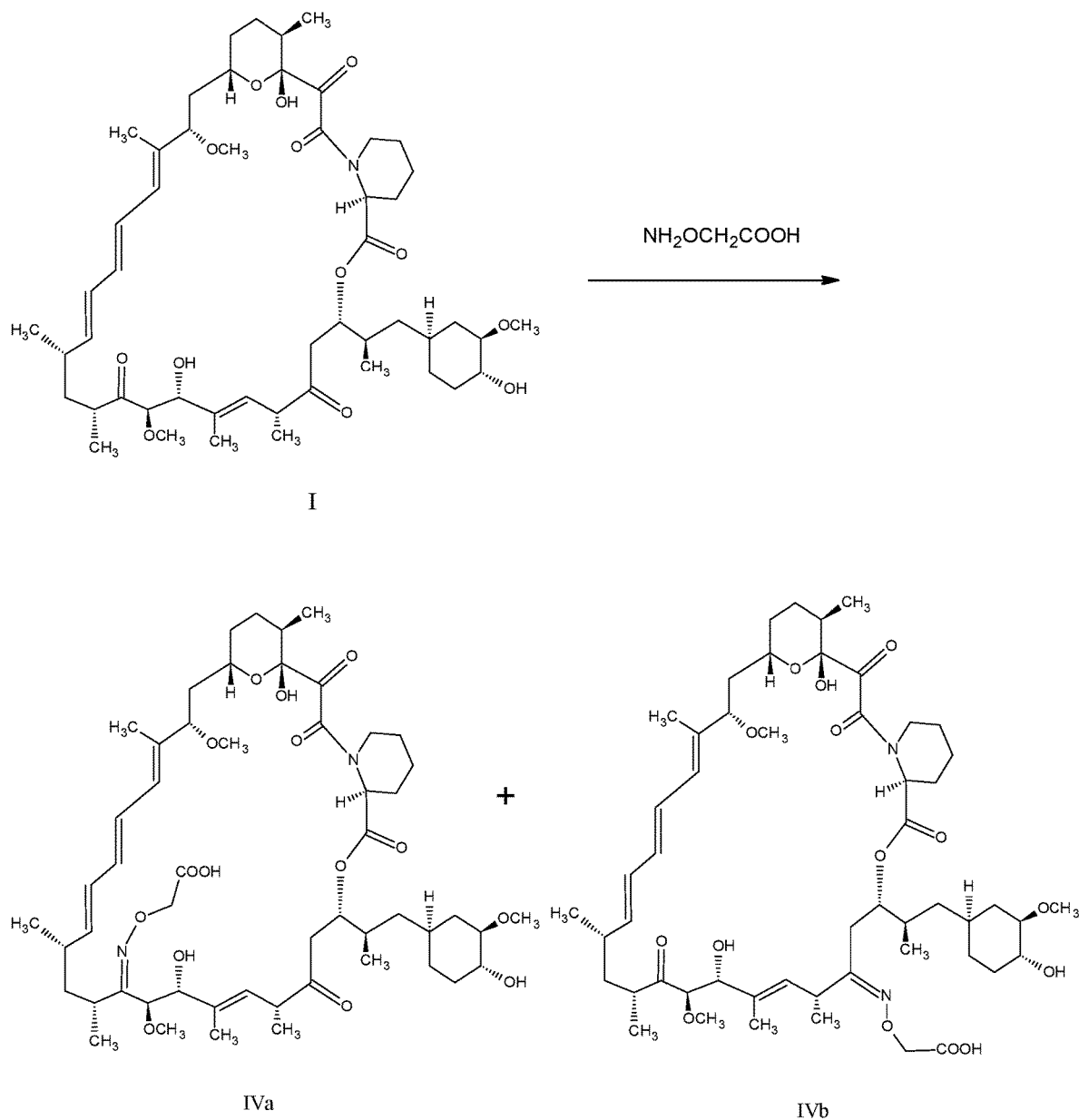
FIG. 6 is a reaction scheme for the preparation of oxime derivatives of sirolimus.

Referring to FIG. 6, sirolimus (I) is reacted with aminooxyacetic acid to form a mixture of oximes of the Formula IVa (representing formation of an oxime at C-26) and IVb (representing formation of an oxime at C-32). The reaction is carried out in an organic solvent such as, for example, an alcohol (e.g., methanol or ethanol), under conditions for forming an oxime. In some examples the temperature during the reaction is about 10° C. to about 30° C., or about 15° C. to about 25° C. The time period of the reaction is about 1 hour to about 30 hours, or about 2 hours to about 24 hours. Compounds IVa and IVb may be separated or the mixture of compounds IVa and IVb may be employed in the next step of the preparation of an immunogen. Separation of IVa and IVb may be carried out by, but not limited to, chromatography (TLC, HPLC, RPLC, HTLC) and gas chromatography, for example.

Figure 7:
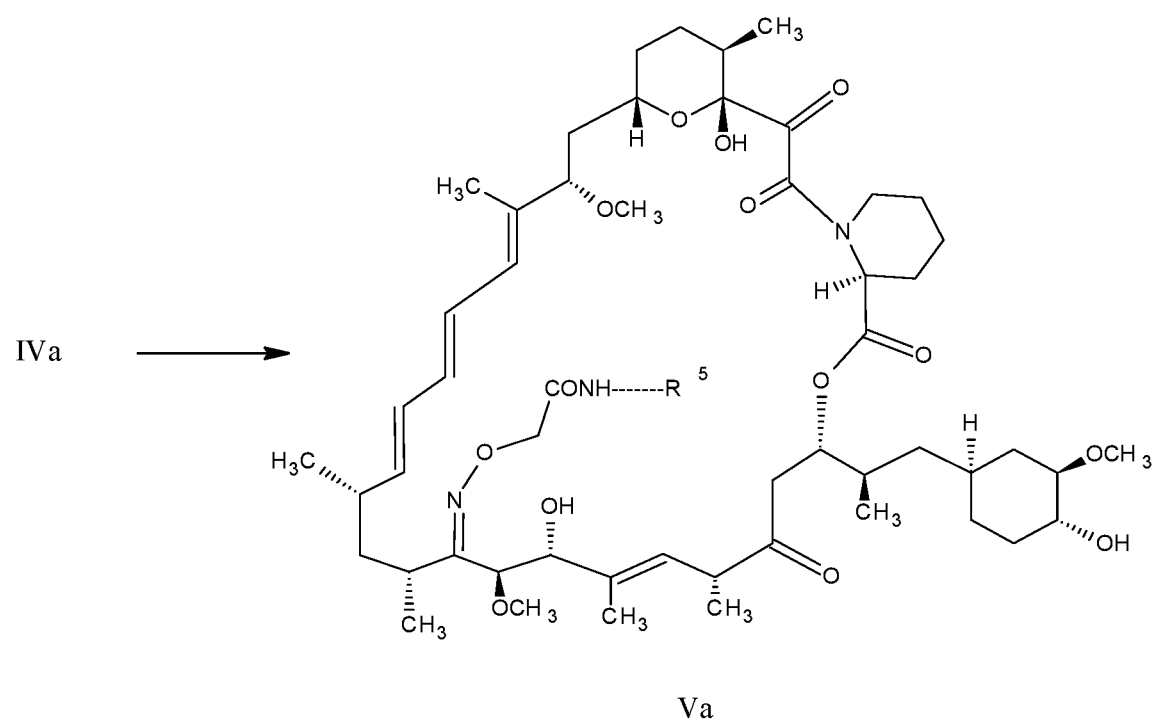
FIG. 7 is a reaction scheme for the preparation of an immunogen from an oxime derivative of sirolimus of FIG. 6.

FIG. 7 depicts, by way of illustration and not limitation, formation of an immunogen from compound IVa. A poly (amino)acid immunogenic carrier ($R^5$ precursor) is combined with compound of IVa to form a compound of the formula Va. The reaction is carried out in an aqueous buffered medium at a pH of about 5.0 to about 7.0, or about 5.5 to about 6.5, or about 6. An activation agent or coupling for facilitating the reaction of the carboxylic acid functionality of Va with an amine group of the $R^5$ precursor is included in the reaction medium. Such coupling agents include, but are not limited to, 1-ethyl-3-(3-dimethylaminopropyl)-carbodiimide (EDAC), N-hydroxysuccinimide (NHS), or N,N,N',N'-tetramethyl-O—(N-succinimidyl)uronium tetrafluoroborate, or combinations of two or more of the above. The reaction is carried out under conditions for forming an amide. In some examples, the reaction medium is an aqueous medium, which may be solely water or may include from 0.1 to about 40 volume percent of a cosolvent, which may be a polar organic solvent such as for example, an amine (e.g., dimethylformamide (DMF)); an alcohol (e.g., ethanol); or an ether (e.g., furan), for example. In some examples the temperature during the reaction is about 15° C. to about 25° C. The time period of the reaction is about 3 hours to about 24 hours, or about 4 hours to about 20 hours, or about 4 hours to about 10 hours, for example. In some examples, by way of illustration and not limitation, the $R^5$ precursor is a protein such as BSA or KLH, for example. An immunogen may also be prepared from compound IVb in a similar manner to that described above for the preparation of immunogen Va. A mixture of compounds IVa and IVb may also be used to prepare a mixture of immunogens.

An anti-tacrolimus antibody is prepared and selected for its binding not only with tacrolimus but also its cross-reaction with sirolimus. The anti-tacrolimus antibody binds to a portion of sirolimus other than that to which the anti-sirolimus antibody binds since domain region D1 of sirolimus is not present in tacrolimus. The portion of sirolimus to which the anti-tacrolimus antibody binds is domain region D2, which is structurally similar to domain region D2' of tacrolimus. The second monoclonal antibody may be prepared using, for example, tacrolimus linked to an immunogenic carrier as an immunogen for antibody preparation in methods described above. Examination of the sirolimus structure by three-dimensional analysis reveals the conformation of regions D1 and D2.

In a specific example, by way of illustration and not limitation, tacrolimus at the C22 position of the tacrolimus molecule is linked, either directly by a bond or through the intermediacy of a linking group, to an immunogenic carrier. In a particular example, by way of illustration and not limitation, the keto group at the C22 position is reacted with an amine to produce an oxime. The amine may be, but is not limited to, carboxymethoxylamine, for example.

In one approach the reaction of tacrolimus with carboxymethoxylamine produces a carboxymethyl oxime. In this particular example, tacrolimus may be reacted with carboxymethoxylamine in an alcoholic medium such as, e.g., methanol, ethanol or propanol, in the presence of a buffer salt such as, e.g., sodium acetate, to give the carboxymethyl oxime. This oxime may be linked to an immunogenic carrier such as, e.g., a high molecular weight protein, which may be, but is not limited to, bovine serum albumin, thyroglobulin, ovalbumin, fibrinogen, or keyhole limpet hemocyanin, for example. In one example, the protein is keyhole limpet hemocyanin.

In an example, a method of preparation of the conjugate of tacrolimus with a high molecular weight protein is as follows: (1) preparation of the carboxymethyl oxime of tacrolimus as described above; (2) activating the carboxymethyl oxime to produce a reactive N-hydroxysuccinimide ester; and (3) reacting the N-hydroxysuccinimide ester with the high molecular weight protein to produce the conjugate. The activation of the carboxymethyl oxime to produce the N-hydroxysuccinimide ester is performed, for example, by using a coupling agent such as a water-soluble carbodiimide such as, for example, 3-(3-dimethylaminopropyl 1-ethyl-3-dimethylaminopropyl)-carbodiimide hydrochloride (EDAC).

The monoclonal antibody that binds to both tacrolimus and sirolimus may be identified, for example, by a screening method, by way of illustration and not limitation, as follows: The assay is a competitive assay that utilizes the antibody conjugated to β-galactosidase (antibody-β-galactosidase conjugate) and a sirolimus or tacrolimus analog coated on the surface of a CrO2 magnetic particle. The assays may be performed on the Siemens DIMENSION® clinical chemistry system using samples containing tacrolimus or sirolimus. The sample is added to a reaction vessel. The antibody-β-galactosidase conjugate reagent is added to the reaction vessel and mixed with the sample. This step allows formation of a complex comprising tacrolimus or sirolimus with the antibody-β-galactosidase conjugate. Next, tacrolimus or sirolimus analog coated $CrO_2$ particle reagent is added to the reaction mixture. For sirolimus, the analog used to coat the $CrO_2$ particles is a mixture of sirolimus-C26 oxime and sirolimus-C32 oxime derivatives as depicted in FIG. 6. For tacrolimus detection, the analog used is FK506-C32-succinate (prepared as described in U.S. Pat. Nos. 5,532,137 and 5,164,495), the relevant disclosure of which is incorporated herein by reference. After incubation to allow tacrolimus or sirolimus analog coated $CrO_2$ particles to scavenge the excess amount of antibody-β-galactosidase conjugate that is not bound to tacrolimus or sirolimus, the $CrO_2$ particles are magnetically separated from the reaction mixture in the vessel and an aliquot of supernatant containing tacrolimus (or sirolimus): antibody-β-galactosidase conjugate complexes is transferred from the reaction vessel to a photometric cuvette containing chlorophenol red-β-D-galactopyranoside (CPRG). The rate of the conversion of CPRG to chlorophenol red (CPR) is measured bichromatically at 577 and 700 nm. This rate is proportional to the concentration of tacrolimus or sirolimus in the sample. Antibody is selected for demonstrating sufficient binding affinity for both tacrolimus and sirolimus based on the concentration of tacrolimus or sirolimus obtained in the assay.

Figure 5:
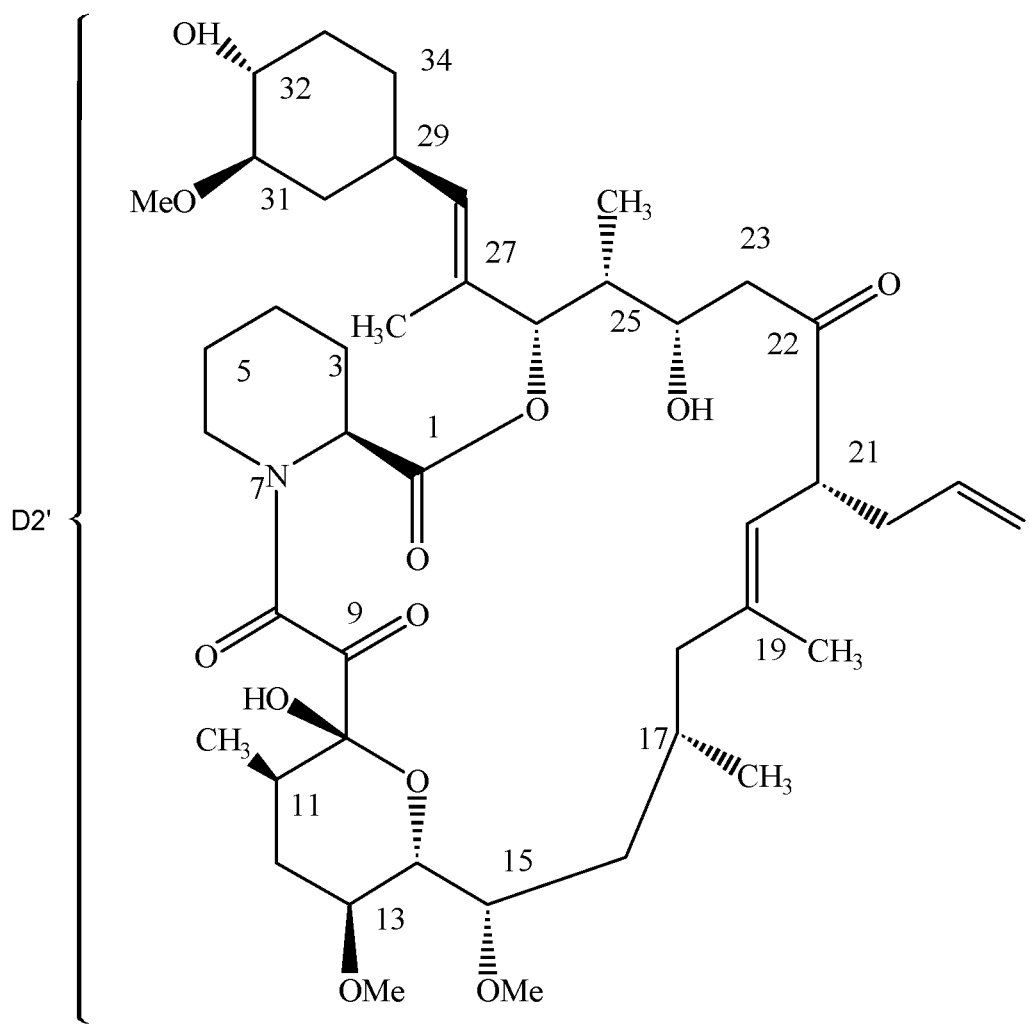
FIG. 5 is the chemical formula of FIG. 3 depicting a portion of the tacrolimus molecule that is structurally similar to that of a portion of sirolimus and of everolimus.

As can be seen from FIG. 5, domain region D2' of tacrolimus is structurally similar to domain region D2 of sirolimus. Tacrolimus may be employed as a compound linked to an immunogenic carrier to form an immunogen where the compound is not sirolimus or a derivative of sirolimus but comprises a moiety (domain region D2' of tacrolimus) that is structurally similar to that of the domain region D2 of sirolimus.

In the screening assay for obtaining anti-tacrolimus antibody that binds also to sirolimus, antibody preparations using an immunogen comprising tacrolimus are screened in an immunoassay to identify one or more antibodies that are highly cross-reactive with sirolimus. This approach is contrary to approaches for antibody selection where antibodies are chosen that have little or no cross-reactivity with molecules other than the molecule used in the immunogen.

As mentioned above, sirolimus and tacrolimus are used by way of example. The above approach may be applied to other small molecules in order to prepare first and second antibodies to carry out a sandwich assay for the small molecules. If an assay antibody in a competitive assay format binds to a unique epitope or domain of the small molecule where the small molecule shares a common domain with, or comprises a domain that is structurally similar to a domain in, another hapten, such hapten can be used to generate an antibody that cross-reacts with the small molecule analyte. In this manner, two antibodies that bind to separate domain regions of the small molecule can be prepared and used in a sandwich assay for the small molecule.

General Description of Assays for a Small Molecule

As mentioned above, examples in accordance with the principles described herein enable a sandwich assay for the determination of a small molecule in a sample suspected of containing the small molecule. In the discussion below, an immunosuppressant drug is used as an example, by way of illustration and not limitation, of a small molecule as defined herein. In the sandwich assay, two monoclonal antibodies are employed, each of which bind at the same time to separate regions of the immunosuppressant drug molecule to form an immunocomplex. Detection of the immunocomplex permits the determination of the immunosuppressant drug in the sample.

The sample to be tested is usually a biological sample. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid. In some examples the sample is whole blood, plasma or serum.

Prior to the assay, or in some instances during the assay, the sample may be subjected to one or more pretreatments to lyse cells and/or to release immunosuppressant drug from endogeneous binding substances. Lysing cells may be accomplished by use of a hemolytic agent, which is a compound or mixture of compounds that disrupts the integrity of the membranes of red blood cells thereby releasing intracellular contents of the cells. Hemolytic agents include, but are not limited to, non-ionic detergents, anionic detergents, amphoteric detergents, low ionic strength aqueous solutions (hypotonic solutions), bacterial agents, and antibodies that cause complement dependent lysis, for example.

Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis (ethoxylate-block-propoxylate) tetrol, IGEPAL®, MERPOL®, poly(ethylene glycol), 2-[ethyl [(heptadecafluorooctyl)-sulfonyl]amino] ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanoliamin, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

The nature and amount or concentration of hemolytic agent employed depends on one or more of the nature of the sample, the nature of the immunosuppressant drug, the nature of the rest of the reagent components, and the reaction conditions, for example. The amount of the hemolytic agent is at least sufficient to cause lysis of red blood cells to release contents of the cells. In some examples the amount of the hemolytic agent is about 0.0001% to about 0.5%, about 0.001% to about 0.4%, about 0.01% to about 0.3%, about 0.01% to about 0.2%, about 0.1% to about 0.3%, about 0.2% to about 0.5%, or about 0.1% to about 0.2%, for example (percent is weight/volume).

The releasing agent is a compound or mixture of compounds that displaces the immunosuppressant drug from endogenous binding moieties. The releasing agent can, and does in many instances, displace metabolites of the immunosuppressant drug from endogenous binding moieties. In many examples the releasing agent has high binding affinity to the endogenous binding proteins so that it readily displaces the immunosuppressant drug, and its metabolites where desired, from endogenous binding proteins. In addition, the releasing agent does not bind to any significant degree to a monoclonal antibody for the drug that is used in an assay. By the phrase "does not bind to any significant degree" is meant that the extent of binding should be low enough so that an accurate assay for the drug may be carried out. The releasing agent, therefore, may be any moiety, either a single compound or a mixture of compounds, which accomplishes the desired result of displacement with no significant binding to an assay antibody.

In some examples the releasing agent is an analog, including structural analogs, of the immunosuppressant drug. An immunosuppressant drug analog is a modified drug that can displace the analogous immunosuppressant drug from a binding protein but does not compete to any substantial degree for a monoclonal antibody for the immunosuppressant drug. The modification provides means to join an immunosuppressant drug analog to another molecule. In an example, the immunosuppressant drug analog may be, for example, the immunosuppressant drug conjugated to another molecule through a linking group. For immunosuppressant drugs that comprise a hydroxy or carboxylic acid functionality, the releasing agent may be an ester of the immunosuppressant drug, which has a high binding affinity for endogenous binding proteins relative to the immunosuppressant drug to be detected and which has no significant binding affinity for an antibody for the immunosuppressant drug. For example, in a determination for tacrolimus, an ester of tacrolimus may be employed as the releasing agent so long as it meets the above requirements. A structural analog is a moiety that has the same or similar structural or spatial characteristics as the immunosuppressant drug such that the structural analog accomplishes the same or similar result as the analog of the immunosuppressant drug. The structural analog may be, for example, another compound that is related to the immunosuppressant drug. For example, in a determination for tacrolimus, an ester of sirolimus may be employed as the releasing agent. The ester may be, for example, a carbamate, a carbonate, an ester of a $C_1$ to $C_6$ carboxylic acid, and the like. See, for example, U.S. Pat. No. 7,186,518, the relevant disclosure of which is incorporated herein by reference. Other examples of releasing agents include [$Thr_2$, $Leu_5$, $D-Hiv_8$, $Leu_{10}$]-cyclosporin A for cyclosporin A, FK506 for sirolimus, sirolimus for FK506, and the like. See, for example, U.S. Pat. No. 6,187,547, the relevant disclosure of which is incorporated herein by reference.

The concentration of the releasing agent in the medium is that sufficient to achieve the desired result of displacing the immunosuppressant drug, and in some instances the metabolites of the immunosuppressant drug, from endogenous binding moieties to render the drug and metabolites accessible for binding to an antibody for the drug as discussed above. The amount or concentration of the releasing agent employed depends on one or more of the nature of the sample, the nature of the immunosuppressant drug, the nature of the drug metabolites, the nature of other reagent components, and the reaction conditions, for example. In some embodiments the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

The assay is an immunoassay, which may be performed either without separation (homogeneous) or with separation (heterogeneous) of any of the assay components or products. The homogeneous or heterogeneous assays are carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, or in the range of about 5 to about 10, or in the range of about 6.5 to about 9.5. The pH will usually be a compromise between optimum binding of the monoclonal antibodies and the immunosuppressant drug, and the pH optimum for other reagents of the assay such as members of the signal producing system, for example.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; for example.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures range from about 5° to about 99° C., or about 15° C. to about 70° C., or about 20° C. to about 45° C. The time period for the incubation is about 0.2 seconds to about 6 hours, or about 2 seconds to about 1 hour, or about 1 to about 5 minutes. The time period depends on the temperature of the medium and the rate of binding of the various reagents, which is determined by the association rate constant, the concentration, the binding constant and dissociation rate constant. Temperatures during measurements range from about 10° C. to about 50° C., or from about 15° C. to about 40° C.

The concentration of immunosuppressant drug analyte that may be assayed generally varies from about $10^{-6}$ to about $10^{-17}$ M, or from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentrations of the various reagents in the assay medium will generally be determined by the concentration range of interest of the immunosuppressant drug analyte. However, the final concentration of each of the reagents is normally determined empirically to optimize the sensitivity of the assay over the range. That is, a variation in concentration of analyte that is of significance should provide an accurately measurable signal difference. Considerations such as the nature of a signal producing system and the nature of the immunosuppressant analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

In the assays discussed above, one or more labels are employed wherein the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the immunosuppressant drug being detected or to an agent that reflects the amount of the immunosuppressant drug to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, as the case may be.

Suitable labels include, by way of illustration and not limitation, enzymes such as β-galactosidase, alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chrome particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members or one or more of the monoclonal antibodies can be bound to a support. A monoclonal antibody may be bound to a solid support in any manner known in the art, provided only that the binding does not substantially interfere with the ability to bind with a region of the immunosuppressant drug. In some examples, the label or other sps member or the monoclonal antibody may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the moiety to be coupled. The linking group may be one as described above for the linking of immunogen to an immunosuppressant drug molecule. Other methods of binding to a support may also be employed. For instance, a solid support may have a coating of a binder for a small molecule such as, for example, avidin or an antibody, where a small molecule such as, e.g., biotin or a hapten, can be bound to the moiety to be coupled or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, and DENDRIMERS, for example. Depending on the type of assay, the support may or may not be suspendable in the medium in which it is employed. Examples, by way of illustration and not limitation, of suspendable supports are polymeric materials such as latex, lipid bilayers or liposomes, oil droplets, cells and hydrogels, and magnetic particles, for example. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), for example; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *Streptococcus, Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chrome particles or latex particles.

The polymer particles can be formed of addition or condensation polymers. The particles will be readily dispersible in an aqueous medium and can be adsorptive or functionalizable so as to permit conjugation to a monoclonal antibody for an immunosuppressant drug, either directly or indirectly through a linking group. The linking group may be one as described above for the linking of immunogens to an immunosuppressant drug molecule. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to one or both of the two different monoclonal antibodies. Bonding of the label to the sbp member may be accomplished by chemical reactions that result in replacing a hydrogen atom of the label with a bond to the monoclonal antibody or may include a linking group between the label and the monoclonal antibody. The linking group may be one as described above for the linking of immunogens to an immunosuppressant drug molecule. Other sps members may also be bound covalently to the monoclonal antibodies. For example, two sps members such as a fluorescer and quencher can each be bound, respectively, to the monoclonal antibodies where the fluorescer is bound to one of the monoclonal antibodies and a quencher is bound to the other of the monoclonal antibodies. When the two different monoclonal antibodies bind to the immunosuppressasnt drug, the formation of a sandwich complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include, but are not limited to, saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems addition of a substrate and/or a cofactor may be necessary.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the sirolimus compound present in a sample. Temperatures during measurements may range from about 10° to about 70° C., or from about 20° to about 45° C., or from about 20° to about 25° C. In one approach standard curves are formed using known concentrations of the analytes to be screened. As discussed above, calibrators and other controls may also be used.

The phrase "measuring the amount of an immunosuppressant drug" refers to the quantitative, semi-quantitative and qualitative determination of the immunosuppressant drug. Methods that are quantitative, semi-quantitative and qualitative, as well as all other methods for determining the immunosuppressant drug, are considered to be methods of measuring the amount of the immunosuppressant drug. For example, a method, which merely detects the presence or absence of the immunosuppressant drug in a sample suspected of containing the immunosuppressant drug, is considered to be included within the scope of the present disclosure. The terms "detecting" and "determining," as well as other common synonyms for measuring, are contemplated within the scope of the present disclosure.

In one example in accordance with the principles described herein, one of the monoclonal antibodies specific for a region of an immunosuppressant drug is bound to a support and the other of the monoclonal antibodies that is specific for a region of the immunosuppressant drug that is spatially separated from the region of the immunosuppressant drug to which the other monoclonal antibodies binds is bound to an sps member such as, for example, a label. The sample suspected of containing the immunosuppressant drug is combined in a suitable medium with the two conjugated monoclonal antibodies and the medium is incubated. Then, the medium is examined for the one or both of the presence and amount of an immunocomplex formed by the two different monoclonal antibodies and the immunosuppressant drug from the sample. The support may or may not be separated from the medium prior to the examination. The presence and/or amount of the immunocomplex is determined by determining the presence and/or amount of the label in the medium or on the support.

In one particular example, a capture assay is employed. In this assay format, one monoclonal antibody is covalently bound to a magnetic particle such as, for example, a chrome (chromium dioxide) particle. The sample is incubated with these particles to allow the immunosuppressant drug in the sample to bind to the monoclonal antibody on the magnetic particle. Subsequently, a second monoclonal antibody conjugated to an enzyme such as, for example, β-galactosidase, is incubated with the magnetic particles. After application of a magnet and washing of the magnetic particles, the amount of enzyme that is bound to the magnetic particles is measured and is directly related to the presence and/or amount of the immunosuppressant drug in the sample. In this approach substrate of the reporter enzyme is added to the final reaction container, and the enzyme activity is measured spectrophotometrically as a change in absorbance over time.

In an alternative approach, the magnetic particle reagent is added in an excess amount, i.e., an amount greater than that required to bind all of the immunosuppressant drug that might be present in the sample. Then, a magnet is applied to separate the magnetic particles from the medium and the magnetic particles are washed and resuspended in assay medium. The enzyme conjugated to the second monoclonal antibody is added and the medium is incubated followed by signal determination as described above.

In another example, by way of illustration and not limitation, chemiluminescent particles are employed, which comprise the chemiluminescent compound associated therewith such as by incorporation therein or attachment thereto. One of the monoclonal antibodies for the immunosuppressant drug is bound to the particles such as through the intermediacy of a polysaccharide coating the particles. The other monoclonal antibody that binds to the immunosuppressant drug is part of a biotin conjugate. Streptavidin is conjugated to a second set of particles having a photosensitizer associated therewith. The chemiluminescent particles are mixed with a sample suspected of containing the immunosuppressant drug and the photosensitizer particles. The reaction medium is incubated to allow the particles to bind to the immunosuppressant drug by virtue of the binding of the monoclonal antibodies to the immunosuppressant drug. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the immunosuppressant drug, it is activated by singlet oxygen and emits luminescence. The medium is then examined for the presence and/or the amount of luminescence or light emitted, the presence thereof being related to the presence and/or amount of the immunosuppressant drug in a sample.

Kits for Conducting Assays

The reagents for conducting a particular assay may be present in a kit useful for conveniently performing an assay for the determination of a small molecule such as, for example, an immunosuppressant drug analyte. In one example, a kit comprises in packaged combination reagents for analyzing for the analyte, the nature of which depend upon the particular assay format. The reagents may include, for example, one or more monoclonal antibodies in accordance with the principles described herein, which may be conjugated to a label or a support. The reagents may each be in separate containers or various reagents can be combined in one or more containers depending on the cross-reactivity and stability of the reagents. The kit can further include other separately packaged reagents for conducting an assay such as additional binding members and ancillary reagents.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method in accordance with the present embodiments as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The designation "first" and "second" is completely arbitrary and is not meant to suggest any order or ranking among any members of a group to which the above language pertains such as, for example, "first and second monoclonal antibodies" or "first monoclonal antibody" and "second monoclonal antibody."

The following examples further describe the specific embodiments of the invention by way of illustration and not limitation and are intended to describe and not to limit the scope of the invention or the claims attached hereto. Parts and percentages disclosed herein are by volume unless otherwise indicated.

EXAMPLES

All chemicals were purchased from the Sigma-Aldrich Company (St. Louis MO) unless otherwise noted.

Testing was carried out using the DIMENSION® RxL analyzer, available from Siemens A G, Newark DE The instrument was employed using enzymatic detection system with sandwich immunoassay format. In the embodiment of the sandwich method used herein and discussed in more detail below, binding between a labeled antibody (Ab) conjugated to an enzyme (conjugate) and sirolimus drug (SIRO) in patient samples and subsequent binding of the resulting immunocomplex with a capture antibody on chrome particles determined the amount of sirolimus in the patient samples. The unbound tag antibody enzyme conjugate was removed automatically by 3-4 mix/wash and magnetic separation cycles. The enzymatic activity from conjugate remaining on the chrome particles was measured and was directly proportional to the amount of sirolimus in the patient sample.

Definitions mg=milligram
g=gram(s)
ng=nanogram(s)
mL=milliliter(s)
μL=microliter(s)
mmol(s)=millimole(s)
μmol=micromolar
° C.=degrees Centigrade
min=minute(s)
sec=second(s)
hr=hour(s)
w/v=weight to volume
v/v=volume to volume
TLC=thin layer chromatography
HPLC=high performance liquid chromatography
UV=ultraviolet
EtOAc=ethyl acetate
MeOH=methanol
DMF=dimethylformamide
DI=deionized
THF=tetrahydrofuran
NHS=N-hydroxysuccinimide
DCC=N,N-dicyclohexyl carbodiimide
BSA=bovine serum albumin
BGG=bovine gamma globulin
mMS=mass spectrometry
SIRO=sirolimus
rotovap=rotary evaporator

Example 1

Preparation of Monoclonal Antibody to Sirolimus

Preparation of C-32-Sirolimus and C-26-Sirolimus Oximes (IVa and IVb) (FIG. 6). To a solution of Sirolimus (I) (653.6 mg, 0.715 mmol) and carboxymethoxyamine hemihydrochloride (234.4 mg, 2.14 mmol) in MeOH (20 mL) is added sodium acetate (181.8 mg, 3.1 mmol). The reaction mixture is stirred at room temperature (23° C.) overnight (18 hr) under a nitrogen atmosphere. TLC analysis indicated that the reaction is completed. (TLC, Silica gel plate, $CH_2Cl_2$/MeOH=9/1). $CH_2Cl_2$ (80 mL) and DI water (20 mL) is added to the mixture, which is stirred 10 min. The $CH_2Cl_2$ layer is separated. The aqueous layer is extracted with $CH_2Cl_2$ (3×30 mL). The combined $CH_2Cl_2$ solutions are washed with DI water (2×40 mL), are dried over Na2SO4, are filtered and are concentrated on a rotovap to give a mixture of C-32-Sirolimus and C-26-Sirolimus oximes (IVa and IVb, 622 mg).

Isolation of C-26-Sirolimus Oxime (IVa) (FIG. 6). An optimal TLC condition (silica gel, EtOAc/Hexanes/MeOH=5/2/1, $R_f$ C-32-oxime=0.59, $R_f$ C-26-oxime=0.51) for the separation of C-32-Sirolimus and C-26-Sirolimus oximes is developed and applied successfully in an BIOTAGE® ISOLERA™ One Flash Chromatography System (John Morris Scientific, Chatswood, NSW). A mixture of C-32-Sirolimus and C-26-Sirolimus oximes (IVa and IVb, 622 mg) is dissolved in $CH_2Cl_2$ (5 mL). The $CH_2Cl_2$ solution is eluted to a cartridge (silica, 50 g SNAP Ultra) associated with the BIOTAGE® ISOLERA™ One Flash Chromatography System. The system is run with mixed solvent in a flow rate of 25 mL/min. All the collected fractions from the cartridge are checked by TLC (EtOAc/Hexanes/MeOH=5/2/1). Base on TLC analysis, the more polar pure fractions ($R_f$ C-26-oxime=0.51) are combined and concentrated to give C-26-Sirolimus oximes (IVa) (197 mg). HPLC-UV analysis of this compound indicates a purity of 95%.

Preparation of C-26-Sirolimus Oxime-BSA Conjugate (Va) ($R^5$=BSA in FIG. 7). To a solution of IVa (167.97 mg, 0.17 mmol) in THF/DMF (8 mL THF, 0.4 mL DMF), NHS (41.8 mg, 0.35 mmol) and DCC (70.9 mg, 0.34 mmol) is added. The reaction mixture is stirred at room temperature under a nitrogen atmosphere and the product NHS ester is slightly less polar than compound IVa in TLC analysis. A white solid formed during the reaction is filtered and then washed with EtOAc. After solvent is removed, the reaction mixture ire-dissolved in EtOAc and filtered; evaporation of solvent afforded a slight yellow solid, which is held under high vacuum for 1 hr.

The activated hapten NHS ester (slight yellow solid) is dissolved in DMF (1 mL) and the solution is added dropwise to a BSA (120 mg) in phosphate buffered saline (PBS) buffer (0.1 M $NaH_2PO_4$/$Na_2HPO_4$, pH 8) (14 mL) in an ice bath. After stirring for 1 hr at room temperature, pH of the solution is adjusted to pH 8 with NaOH (1N) and the mixture is stirred in a cold room (4° C.) overnight. The BSA conjugate is purified through an equilibrated SEPHADEX® G-25 column (C26×70) with PBS buffer (0.1 M $NaH_2PO_4$/$Na_2PO_4$, pH 7), and eluted with same PBS buffer. A UV detector at 280 nm is used to monitor the eluted fractions from the column. A clean separation between BSA conjugate and the unconjugated hapten IVa is observed. Fractions containing BSA conjugate (Va) are pooled to a total of 57 mL, and the concentration of the Va is determined to be 2.52 mg/mL by the BCA Protein Concentration Assay (Pierce Biotechnology, Rockford IL).

Preparation of Monoclonal Antibody that Binds to Domain D1 of Sirolimus. Monoclonal antibodies that bind to domain D1 of the sirolimus molecule are prepared as follows. The immunogen is the BSA conjugate Va prepared as described above. This immunogen is used to immunize Balb/c mice. The first immunization is 25 μg in a volume of 200 μl with monophosphoryl lipid A and synthetic trehalose dicorynomycolate adjuvant (RIBI MPL+TDM Emulsion, RIBI ImmunoChem Research Inc., Hamilton MT) intraperitoneally. Five weeks later a boost immunization is given with 25 μg of the immunogen in 200 μl of monophosphoryl lipid A and synthetic trehalose dicorynomycolate adjuvant intraperitoneally. Subsequently, after another 8 weeks, a prefusion boost is given of the 25 µg of the immunogen in 200 µl of Hanks' Balanced Salt Solution intravenously and intraperitoneally.

Three days later, fusion is performed by standard methods using a nonsecreting murine myeloma designated P3x63-AG8.653. Cloning is carried out by standard methods.

The clones are screened by the following reverse ELISA immunoassay procedure according to the following protocol. Plates are coated with polyclonal goat anti-mouse IgG (IgG+IgA+IgM) (Zymed Laboratories, South San Francisco CA) at 5 µg/ml in phosphate buffered saline at 100 µl per well. Plate coating is performed for 2 hours or more at room temperature or overnight at about 4° C. The plates are then flicked dry and blocked with 300 µl per well of blocking buffer diluent (0.5% bovine serum albumin, 0.05% TWEEN® 20 in PBS). Plate blocking is performed by incubation for 15 minutes or more at room temperature with plate shaking. The plates are then flicked dry. The monoclonal antibody to be screened is then added to each well as follows: 50 µl per well of blocking buffer diluent was added along with 50 µl per well culture supernatant transferred from the corresponding well in the fusion growth plate. Incubation is for about 1 hour at room temperature with shaking. The plate is washed using a TITERTECK PLUS® plate washer with S20 stacker with the washing buffer being PBS with 0.05% TWEEN® 20. An enzyme conjugate of sirolimus covalently coupled to glucose-6-phosphate dehydrogenase diluted in blocking buffer diluent to 1:4000 is added at 100 µl per well. Incubation is performed for about 1 hour at room temperature with shaking. The plate is then washed and a chromogenic solution is added at a volume of 100 µl per well. The chromogenic solution contains 0.593 mM p-iodonitrotetrazolium violet, 0.02 M NAD, 0.033 M glucose-6-phosphate, 0.055 M Tris, 0.02% sodium azide, and a 1:4000 dilution of diaphorase (lipoyl dehydrogenase). BSA is present at 1% (vol/vol) of a 5% w/vol BSA solution. BSA is used to help prevent rapid precipitation of reduced p-iodonitrotetrazolium violet.

From the screening a hybridoma producing a suitable monoclonal antibody that binds to domain D1 of sirolimus is selected.

Preparation of hemolytic pretreatment solution. This pretreatment solution contains 5 µg/mL of FK506, 6.8 mg/mL PIPES™ 1.5 sodium salt, 0.3 mg/mL EDTA Disodium, 1.0 mg/mL Saponin, 0.2% PROCLIN® 300, 0.024 mg/mL Neomycin sulfate and 0.99 mg/mL NaN3, pH 6.5. The FK506 concentration in the final reaction mixture is 1.1 µg/mL.

Preparation of Monoclonal Antibody that Binds to Tacrolimus and Sirolimus

Preparation of Tacrolimus-Keyhole Limpet Hemocyanin Conjugates. To a solution of tacrolimus monooxime (32.3 mg, 36.8 µmol) in 1.05 mL of anhydrous dimethylformamide is added 1-ethyl-3-(3-dimethylaminopropyl)carbodiimide hydrochloride (EDAC) (11 mg, 57.4 µM, 1.5 equiv.) and N-hydroxysuccinimide (7.3 mg, 63.4 µM, 1.7 equiv.). Linkage is at the C22 position of the tacrolimus molecule. The reaction is stirred at room temperature for 1 hour under argon. The mixture is then added dropwise via a syringe to a solution of keyhole limpet hemocyanin (74 mg, 54% pure) in 5.0 mL of phosphate buffered saline (0.1 M, pH 8.0) and 0.25 mL of dimethylformamide. After stirring at room temperature for 2 hours, the resulting suspension is dialyzed (1×4 L, 4° C., 2 hours) against PBS (phosphate buffered saline) (10 mM, pH 7.0).

The resulting mixture is then extracted 3 times with methylene chloride to remove any trace amount of unreacted tacrolimus monooximes. Quantitative analysis of the mixture is conducted using bicinchoninic acid (BCA) protein assay solution to give 50 mg of immunogen in 8 ml of PBS (10 mM, pH 7.0).

Determination of the hapten number using the TNBS method (A.F.S.A. Habeeb, Anal. Biochem. 14:328 (1966)) gives a hapten number of 1300. The immunogen is immediately frozen using a dry ice-acetone bath and kept at −20° C. for storage.

An immunogen mixture containing three positional isomers of tacrolimus (KLH linked at position C32, KLH linked at position C24 and KLH linked at positions C32 and C24) is prepared as follows: Tacrolimus (301.3 mg) in a round bottomed flask is dried in vacuum for 1.5 hours. To the flask is added a stirrer bar, succinic anhydride (568.2 mg), 4-(dimethylamino)pyridine (46.3 mg), dichloromethane (2 mL, anhydrous) and pyridine (2.093 mL). The reaction mixture is stirred at room temperature (24° C.) under nitrogen atmosphere for 24.5 hours. Three positional isomers are the products of this reaction: tacrolimus-32-succinate, tacrolimus-24-succinate and tacrolimus-24, 32-di-succinate. Once reaction is stopped, solvent is removed by rotary evaporation and the product is dried further by vacuum pump for two hours.

To a vial is added the tacrolimus-succinate mixture from above (2.5 mg, 2.8 µmoles), N-hydroxysuccinimide (1.0 mg, 8.7 µmoles) and anhydrous acetonitrile (250 µL). The mixture is capped and stirred at room temperature. To the stirring mixture is added N,N-dicyclohexylcarbodiimide (3.0 mg, 15 µmoles). The vial is capped and the mixture was stirred at room temperature.

After 2 hours, the mixture is evaporated to dryness. The resulting material is dissolved in anhydrous N,N-dimethylformamide (250 µL). This is the working solution of activated FK506-succinate.

In a 20 mL vial is added a solution of KLH (8 mg) in 8 mL of 10 mM phosphate buffer pH 8, and DMF (1.5 mL). The mixture is chilled to about 4° C. and 200 µL of the working solution from above is added dropwise with stirring to the chilled solution. The mixture is stirred for 16-24 hours at 4° C. and then is diluted to 30 mL with water, desalted with two CENTRICON® 30 filters, and reconstituted with fresh water 3 more times. The final material is diluted to 10 mL with water. Protein concentration is determined by BCA protein assay method.

Preparation of Monoclonal Antibody to Tacrolimus and Sirolimus. Monoclonal antibody that binds to both tacrolimus and sirolimus are prepared as follows. The immunogen is tacrolimus-keyhole limpet hemocyanin conjugate prepared as described above. This immunogen is used to immunize Balb/c mice. The first immunization is 25 µg in a volume of 200 µl with monophosphoryl lipid A and synthetic trehalose dicorynomycolate adjuvant (RIBI MPL+TDM Emulsion, RIBI ImmunoChem Research Inc., Hamilton MT) intraperitoneally. Five weeks later a boost immunization is given with 25 µg of the immunogen in 200 µl of monophosphoryl lipid A and synthetic trehalose dicorynomycolate adjuvant intraperitoneally. Subsequently, after another 8 weeks, a prefusion boost is given of the 25 µg of the immunogen in 200 µl of Hanks' Balanced Salt Solution intravenously and intraperitoneally.

Three days later, fusion is performed by standard methods using a non-secreting murine myeloma designated P3x63-AG8.653. Cloning is carried out by standard methods.

The clones were screened by the following reverse ELISA immunoassay procedure according to the following protocol. Plates are coated with polyclonal goat anti-mouse IgG (IgG+IgA+IgM) (Zymed Laboratories, South San Francisco CA) at 5 µg/ml in phosphate buffered saline at 100 µl per well. Plate coating is performed for 2 hours or more at room temperature or overnight at about 4° C.; the plates could be stored wrapped in film at about 4° C. for several days. The plates are then flicked dry and blocked with 300 µl per well of blocking buffer diluent (0.5% bovine serum albumin, 0.05% Tween® 20 in PBS). Plate blocking is performed by incubation for 15 minutes or more at room temperature with plate shaking. The plates are then flicked dry. The monoclonal antibody to be screened is then added to each well as follows: 50 µl per well of blocking buffer diluent is added along with 50 µl per well culture supernatant transferred from the corresponding well in the fusion growth plate. Incubation is for about 1 hour at room temperature with shaking. The plate is washed using a TITERTECK PLUS® plate washer with S20 stacker with the washing buffer being PBS with 0.05% TWEEN® 20. An enzyme conjugate of tacrolimus covalently coupled to glucose-6-phosphate dehydrogenase diluted in blocking buffer diluent to 1:4000 is added at 100 µl per well. Incubation is performed for about 1 hour at room temperature with shaking. The plate is then washed and a chromogenic solution is added at a volume of 100 µl per well. The chromogenic solution contains 0.593 mM p-iodonitrotetrazolium violet, 0.02 M NAD, 0.033 M glucose-6-phosphate, 0.055 M Tris, 0.02% sodium azide, and a 1:4000 dilution of diaphorase (lipoyl dehydrogenase). BSA is present at 1% (vol/vol) of a 5% w/vol BSA solution. BSA is used to help prevent rapid precipitation of reduced p-iodonitrotetrazolium violet.

From the screening a hybridoma producing a suitable monoclonal antibody is selected. This monoclonal is designated as the tag antibody because the antibody binds to both sirolimus and tacrolimus.

Example 2

Determination of Sirolimus Using Automated Chrome Particle Sandwich Assay

Preparation of anti-sirolimus $F(ab')_2$-$\beta$-galactosidase conjugate using a monoclonal antibody that binds to domain D1 of sirolimus. Monoclonal anti-sirolimus antibody that binds to domain D1 of sirolimus (prepared as described above in Example 1) is fragmented to $F(ab')_2$ using lysyl-endopeptidase (Wako, Richmond, VA) digestion and then is conjugated to $\beta$-galactosidase using a standard heterobifunctional SMCC (succinimidyl trans-4-(N-maleimidylmethyl)cyclohexane-1-carboxylate) linker according to known techniques. The antibody conjugate solution contains approximately 2.0 µg/mL anti-sirolimus antibody-$\beta$-galactosidase conjugate, 30 mg/mL protease free bovine serum albumin, 0.126 mg/mL $MgCl_2$, 0.03 mL/mL of ethylene glycol, 24.5 mg/mL HEPES, 38.5 mg/mL Na HEPES, 50 mg/mL NaCl and beta-gal mutein (inactivated beta-galactosidase), pH 7.8.

Magnetic chrome particle preparation. Chrome particles (immunoassay solid phase) are prepared by conjugating a monoclonal antibody that binds to domain D1 of sirolimus (prepared as described above in Example 1 using as an immunogen C-26-Sirolimus Oxime-BSA Conjugate (Va) ($R^5$=BSA in FIG. 6)) to glutaraldehyde coated chromium dioxide particles. The chrome reagent contains chrome particles and 60.4 mg/mL trehalose dihydrate and 7.2 mg/mL polyethylene glycol (PEG) 8000. Three chrome particle concentrations, namely 5, 2.5, and 1.67 mg/mL, are used in the study.

Sandwich sirolimus Assay. The principle and operation of the Sandwich assay for sirolimus is as follows: A whole blood sample (50 µL) containing sirolimus is combined with a hemolytic pretreatment reagent prepared as described above in a reaction vessel on the DIMENSION® RxL analyzer. The whole blood is sampled from a standard cup by first mixing the blood with the ultrasonic sample probe. The mixing of whole blood sample with the pretreatment solution ensures the hemolysis of the whole blood and the displacement of the protein-bound sirolimus molecules from their binding domains.

Anti-sirolimus $F(ab')_2$-$\beta$-galactosidase conjugate prepared using the monoclonal antibody that binds to the D1 domain of sirolimus (50 µL) is added to the reaction vessels and the mixture is held for a period of time (35 sec) and at a temperature of 43° C. to allow sirolimus, if present, to react with the antibody enzyme conjugate. Chrome particles with immobilized monoclonal antibody that binds to both tacrolimus and sirolimus are added (50 µL) to the reaction vessels and are allowed to bind the anti-sirolimus $F(ab')_2$-$\beta$-galactosidase complex to form a sandwich. This reaction mixture is incubated for 14 min at a temperature of 43° C. before the automated magnetic separation, mix and wash cycles begin on the DIMENSION® instrument. A total of 4 separation/wash cycles are employed to remove the unbound anti-sirolimus $F(ab')_2$-$\beta$-galactosidase conjugate and debris from sample. The automated chrome washes are conducted on board using Chemistry Wash solution at pH 8.0 in HEPES buffer, both of which were provided for the DIMENSION® Heterogeneous Immunoassay Module. The washed chrome particles are then re-suspended in the Chemistry Wash solution by ultrasound mixing and a portion (54 µL) of the suspended chrome particles are transferred to a photometric cuvette to mix with a $\beta$-galactosidase substrate solution (chlorophenol red-$\beta$-D-galactopyranoside, or CPRG). The sirolimus bound to the anti-sirolimus $F(ab')_2$-$\beta$-galactosidase conjugate on the chrome particle surface is detected by measuring the enzymatic rate of the conjugate in the presence of CPRG. The rate for each reaction vessel is measured bichromatically at 577 and 700 nm. The results indicate successful detection of sirolimus.

Example 3

Determination of Sirolimus Using Automated ELISA Sandwich Assay

Sandwich enzyme-linked immunosorbent assay (ELISA) for sirolimus. The following steps are employed: Step 1: 50 µL of purified monoclonal antibody that binds to domain D1 of sirolimus (prepared as described above in Example 1 using as an immunogen C-26-Sirolimus Oxime-BSA Conjugate (Va) ($R^5$=BSA in FIG. 6)) (10 µg/mL in PBS) is coated on ELISA plates overnight at 4° C. Plates are washed using MILLI-Q® water (Millipore Corporation, Billerica MA) containing 0.05% TWEEN® 20. Step 2: 200 µL of PCT Blocker solution (0.5% Casein (milk protein) in phosphate buffer containing 0.05% TWEEN® 20) is added to each well and the media are incubated at room temp for 30 min. Plates are washed using MILLI-Q® water containing 0.05% TWEEN® 20. Step 3: 50 µL of desired concentration of sirolimus diluted in PBS is added to the respective wells and the media are incubated at room temperature for 30 min. Plates are washed using MILLI-Q® water containing 0.05% TWEEN® 20. Sirolimus drug concentrations tested are 0, 0.01, 0.02, 0.04, 0.08, 0.16, 0.31, 0.63, 1.25, 2.50, 5.0 and 10.0 ng/mL, respectively. Step 4: The anti-sirolimus F(ab')$_2$-β-galactosidase conjugate prepared using the monoclonal antibody that binds to both tacrolimus and to sirolimus (prepared in a manner similar to that described above) (1:300 diluted in PCT Blocker solution) is added and the media are incubated at room temperature for 30 min. Plates are washed using MILLI-Q® water containing 0.05% TWEEN® 20. Step 5: β-galactosidase substrate solution CPRG is added to each well (100 μL/well). Step 6: The wells are read in plate reader at 577 nm every minute for 20 min. The results indicate successful detection of sirolimus.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of designing monoclonal antibodies for a sandwich assay for sirolimus, wherein sirolimus has spatially separate binding portions such that two different antibodies can bind simultaneously to the same sirolimus molecule without interfering with the binding of each other to form a three-member complex, the method comprising:
    immunizing a first antibody-producing animal with a first immunogen comprising sirolimus linked at carbon atom 26 and/or 32 through an oxime functionality to an immunogenic carrier, wherein the immunogenic carrier of the first immunogen is selected from the group consisting of bovine serum albumin (BSA), keyhole limpet hemocyanin (KLH), egg ovalbumin, bovine gamma globulin (BGG), thyroglobulin, ovalbumin, fibrinogen, and a polysaccharide;
    isolating antibody-producing spleen cells from the first antibody-producing animal;
    selecting at least one antibody-producing spleen cell that secretes a first monoclonal antibody;
    preparing a first hybrid cell line by fusing the selected antibody-producing spleen cell(s) from the first antibody-producing animal with an appropriate fusion partner, whereby the first hybrid cell line secretes the first monoclonal antibody;
    immunizing a second antibody-producing animal with a second immunogen comprising tacrolimus linked to an immunogenic carrier at ring atom 22 for eliciting antibodies, and wherein the immunogenic carrier of the second immunogen is selected from the group consisting of bovine serum albumin (BSA), keyhole limpet hemocyanin (KLH), thyroglobulin, ovalbumin, and fibrinogen;
    isolating antibody-producing spleen cells from the second antibody-producing animal;
    selecting at least one antibody-producing spleen cell that secretes a second monoclonal antibody that binds specifically to sirolimus in a portion other than the domain to which the first monoclonal antibody binds; and
    preparing a second hybrid cell line by fusing the selected antibody-producing spleen cell(s) from the second antibody-producing animal with an appropriate fusion partner, whereby the second hybrid cell line secretes the second monoclonal antibody.

2. The method of claim 1, wherein the step of selecting at least one antibody-producing spleen cell that secretes a first monoclonal antibody is further defined as selecting at least one antibody-producing spleen cell that secretes a first monoclonal antibody that binds specifically to a binding domain extending approximately from ring atom 15 to ring atom 21.

3. The method of claim 1, wherein the first immunogen comprises sirolimus linked at carbon atom 26 through the oxime functionality to the immunogenic carrier.

4. The method of claim 1, wherein the first immunogen comprises sirolimus linked at carbon atom 32 through the oxime functionality to the immunogenic carrier.

5. The method of claim 1, wherein the first immunogen comprises a mixture of sirolimus linked at carbon atom 26 through the oxime functionality to the immunogenic carrier and sirolimus linked at carbon atom 32 through the oxime functionality to the immunogenic carrier.

6. The method of claim 1, wherein the immunogenic carrier of at least one of the first and second immunogens is BSA.

7. The method of claim 1, wherein the immunogenic carrier of at least one of the first and second immunogens is KLH.

8. The method of claim 1, wherein the first immunogen comprises formula Va:

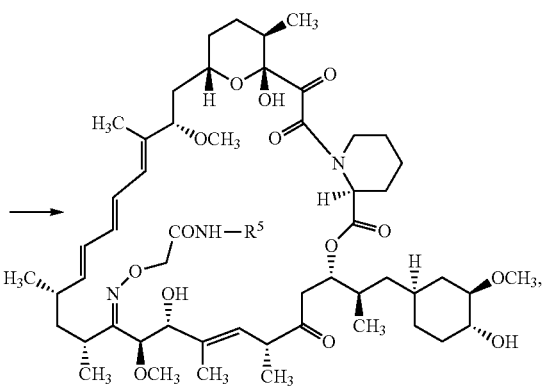

wherein $R^5$ is BSA or KLH.

9. The method of claim 1, wherein the first monoclonal antibody exhibits substantially no binding affinity for tacrolimus.

10. The method of claim 1, further comprising the step of attaching a detectable label to one of the first and second monoclonal antibodies, wherein the detectable label is selected from the group consisting of a fluorescer, a radiolabel, an enzyme, a chemiluminescer, a photosensitizer, and combinations thereof.

11. The method of claim 1, further comprising the step of binding one of the first monoclonal antibody and the second monoclonal antibody to a support.

* * * * *